Figure 1:
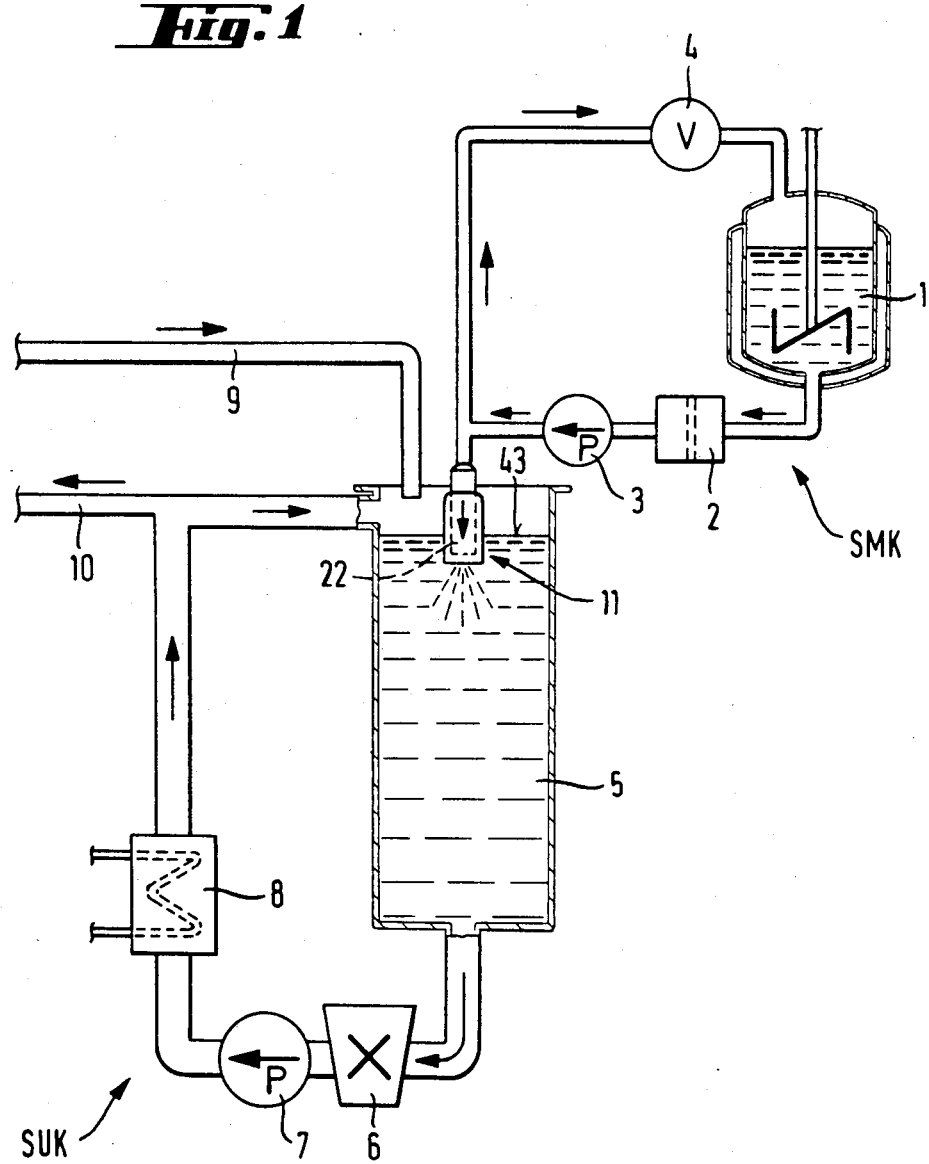

United States Patent [19]

Punzar et al.

[11] Patent Number: 4,744,959
[45] Date of Patent: May 17, 1988

[54] APPARATUS FOR PRODUCING A SUSPENSION OF CYANURIC CHLORIDE IN WATER, OR FOR REACTING CYANURIC CHLORIDE WITH AMMONIA OR WITH AMINES

[75] Inventors: Marianne Punzar, Bottmingen; Franz Marti, Dornach; Robert Mercier, Basel, Paul Tobler; Rudolf Büttiker, both of Riehen, all of Switzerland

[73] Assignee: Ciba-Geigy AG, Basel, Switzerland

[21] Appl. No.: 933,622

[22] Filed: Nov. 21, 1986

Related U.S. Application Data

[62] Division of Ser. No. 710,621, Oct. 30, 1984, Pat. No. 4,678,852, which is a division of Ser. No. 493,920, May 12, 1983, Pat. No. 4,552,959.

[30] Foreign Application Priority Data

May 18, 1982 [CH] Switzerland ............... 3082/82
May 24, 1982 [CH] Switzerland ............... 3184/82

[51] Int. Cl.$^4$ .................. C07D 251/28; B01F 5/04
[52] U.S. Cl. .................. 422/231; 422/235; 422/250; 366/148; 366/167
[58] Field of Search ............ 422/129, 231, 235, 245, 422/250; 144/5, 82, 285, 286; 366/148, 167

[56] References Cited

U.S. PATENT DOCUMENTS

| | | | |
|---|---|---|---|
| 2,779,763 | 1/1957 | Huemer | 260/249.7 |
| 3,575,880 | 4/1971 | Wojohn et al. | 252/311 |
| 3,831,644 | 8/1974 | Berg et al. | 141/82 |
| 3,900,292 | 8/1975 | Fairchild | 422/245 |
| 4,271,297 | 6/1981 | Hentschel et al. | 251/28 |
| 4,271,298 | 6/1981 | Hentschel et al. | 544/190 |
| 4,275,203 | 6/1981 | Hentschel et al. | 544/194 |
| 4,281,123 | 7/1981 | Hentschel et al. | 544/194 |
| 4,377,344 | 3/1983 | Hentschel et al. | 366/173 |

FOREIGN PATENT DOCUMENTS

| | | |
|---|---|---|
| 1670731 | 1/1974 | Fed. Rep. of Germany . |
| 2551164 | 5/1977 | Fed. Rep. of Germany . |
| 2850242 | 6/1980 | Fed. Rep. of Germany . |
| 2850331 | 6/1980 | Fed. Rep. of Germany . |

Primary Examiner—David L. Lacey
Attorney, Agent, or Firm—Wenderoth, Lind & Ponack

[57] ABSTRACT

A process and an apparatus used to produce a suspension of cyanuric chloride in water, or to react cyanuric chloride with ammonia or with amines. It is possible to produce cyanuric chloride suspensions in water which have a mean particle size of below 20 μm, and a concentration of higher than 20% by weight of cyanuric chloride.

10 Claims, 3 Drawing Sheets

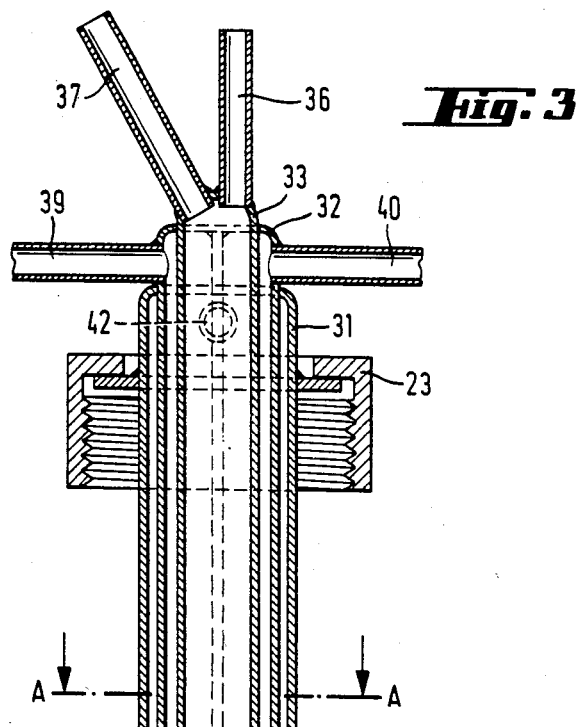
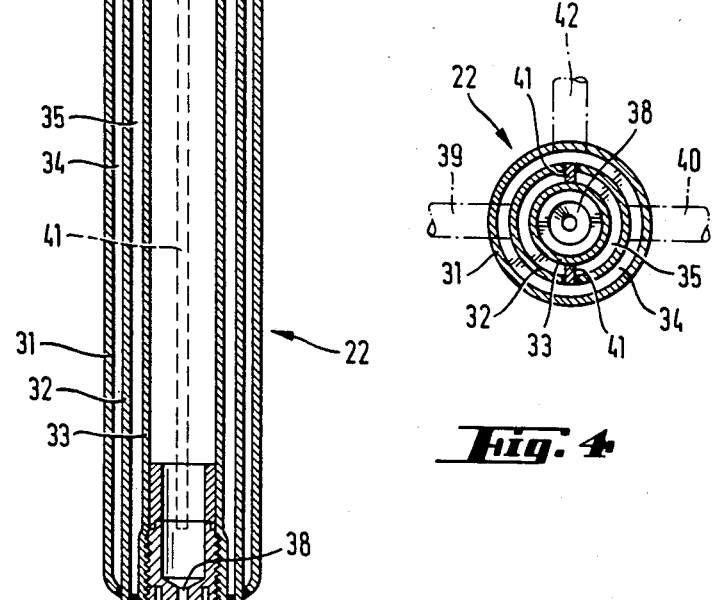

APPARATUS FOR PRODUCING A SUSPENSION OF CYANURIC CHLORIDE IN WATER, OR FOR REACTING CYANURIC CHLORIDE WITH AMMONIA OR WITH AMINES

This application is a division of application Ser. No. 710,621, filed Oct. 30, 1984 (now U.S. Pat. No. 4,678,852), which is a division of application Ser. No. 493,920, filed May 12, 1983 (now U.S. Pat. No. 4,552,959).

The invention relates to a process and an apparatus for producing a suspension of cyanuric chloride in water, or for reacting cyanuric chloride with ammonia or with amines.

Processes for producing a suspension of cyanuric chloride in water have been known for a long time. Thus the German Auslegeschrift No. 1,670,731 describes a process in which melted cyanuric chloride is poured into water. This process is carried out, for example, by producing at the inside wall of a vertically standing cylinder a flow of water, and feeding in the melted cyanuric chloride, at the top end of the cylinder, through a heatable nozzle suitable for spraying. The process has however certain disadvantages. There are problems, for example, in that a layer of solid cyanuric chloride readily forms on the surface of the water; and in that it is not possible with this process to produce a cyanuric chloride suspension having a mean particle size of less than 20 $\mu$m. And furthermore a part of the cyanuric chloride sublimes in the stated device, a factor which can easily lead to the nozzle becoming blocked.

A process for producing suspensions of cyanuric chloride in water is described in the German Auslegeschrift No. 2,850,242. In this process, liquid cyanuric chloride is sprayed through a spray nozzle, situated at the top of a tubular container, into this container; this tubular container is closed or closable at the top end, and it tapers downwards in a convex manner to the point where a discharge outlet is situated; the water in the apparatus emerges from one or more nozzles located above the convex section, and forms a liquid layer along the whole length of the chamber walls as far as the nozzle for the cyanuric chloride. This process too is not able to completely satisfy the requirements, since the small particle size of the cyanuric chloride in a resulting suspension, which is frequently desired in practice, cannot be obtained by this method. Furthermore, it is not possible by this process to produce a finely divided suspension of fairly high concentration, for example containing more than 20% by weight of cyanuric chloride, because incrustations occur at higher concentration. And, finally, this process requires a special reaction vessel.

A process for the reaction of melted cyanuric chloride with amines has moreover already been described in the German Auslegeschrift No. 2,850,331. The special reaction vessel described above is however necessary also for this process.

It was the object of the present invention to provide a process which would avoid to the greatest possible extent the mentioned disadvantages of the known processes. The novel process would in particular make it possible to produce a suspension of cyanuric chloride in water, which suspension would have a mean particle size of below 20 $\mu$m and a concentration of more than 20% by weight of cyanuric chloride.

The said requirements are satisfied by the process according to the invention. It is now possible by virtue of this process to produce for example 30% suspensions of cyanuric chloride in water with a particle size of between 0 and 20 $\mu$m. In the preferred embodiment, there is merely used a particularly suitable spray device which, however, can be used in the customary reaction vessels. Finally, it is possible by the process according to the invention to react, in a simple manner, cyanuric chloride directly with aqueous solutions or suspensions of ammonia or amines.

Subject matter of the present invention is a process for producing a suspension of cyanuric chloride in water, or for reacting cyanuric chloride with ammonia or with amines, by bringing melted cyanuric chloride into contact with water or with an aqueous ammonia or amine solution or suspension, which process comprises spraying through a nozzle, which is immersed in the liquid, melted cyanuric chloride into water or into an aqueous ammonia or amine solution or suspension.

The temperature of the cyanuric chloride melt is above the melting point of the cyanuric chloride and is about 146° C. to about 190° C., preferably between 155° and 180° C.; and the temperature of the water or of the amine solution or suspension, before commencement of the addition of the cyanuric chloride, is between 0° and 40° C., preferably between 0° and 25° C.

Suitable amines for the process according to the invention are aliphatic, aromatic or heterocyclic amines, that is, primary and secondary amines, for example: methylamine, dimethylamine, ethylamine, diethylamine, propylamine, isopropylamine, n-butylamine, isobutylamine, tert-butylamine, 3-methoxypropylamine, $\alpha$-aminoisobutyronitrile, aniline, n-ethylaniline or 2-, 3- or 4-aminopyridine, and in particular dyes or optical brighteners, as well as intermediates thereof, which contain primary or secondary amino groups. They are, for example, naphthylaminesulfonic acids, aminonaphtholsulfonic acids, aminoanthraquinones, aminostilbenesulfonic acids or azo or anthraquinone dyes having at least one unsubstituted or monosubstituted amino group.

The amines and the cyanuric chloride are generally used in about stoichiometric amounts, but a slight excess, for example, up to 10%, of one of the components is also possible.

The weight ratio of ammonia or amines to water can vary within a wide range. In general, 5 to 50%, preferably 10 to 40%, solutions or suspensions are used.

If desired or necessary, a customary dispersing agent can be added to the aqueous suspension of the amines, in order to improve the fine distribution of the amine.

The melted cyanuric chloride is preferably sprayed through a heated nozzle immersed in the liquid. By means of a special construction of the spray nozzle, which is described in the following, this nozzle can be started and stopped in the immersed position; and the heating system of the nozzle does not transfer too much heat to the reaction solution or suspension. It is advisable to have the conditions during spraying adjusted to ensure that the mean particle size of the cyanuric chloride after spraying is between 0.5 and 200 $\mu$m, preferably between 1 and 100 $\mu$m, and especially between 5 and 20 $\mu$m.

The process according to the invention can be carried out discontinuously or, preferably, continuously.

Fine-granular suspensions containing more than 50% by weight of cyanuric chloride can be produced by the process according to the present invention. Depending on the given conditions, the primary particles can indeed coagulate to again form loose agglomerates: these are broken up however even by slight mechanical stressing. Tedious grinding operations, as occur in the case of the processes of the prior art already described, are not necessary. There are obtained by the process of the present invention suspensions which have a particle size of 5 to 20 µm, and which are virtually free from hydrolysis products.

When the cyanuric chloride is sprayed into aqueous solutions or suspensions of ammonia or amines, instead of into water, there are obtained directly the reaction products of cyanuric chloride with 1 or 2 mols of amine, depending on the emloyed quantity ratios.

Figure 2:
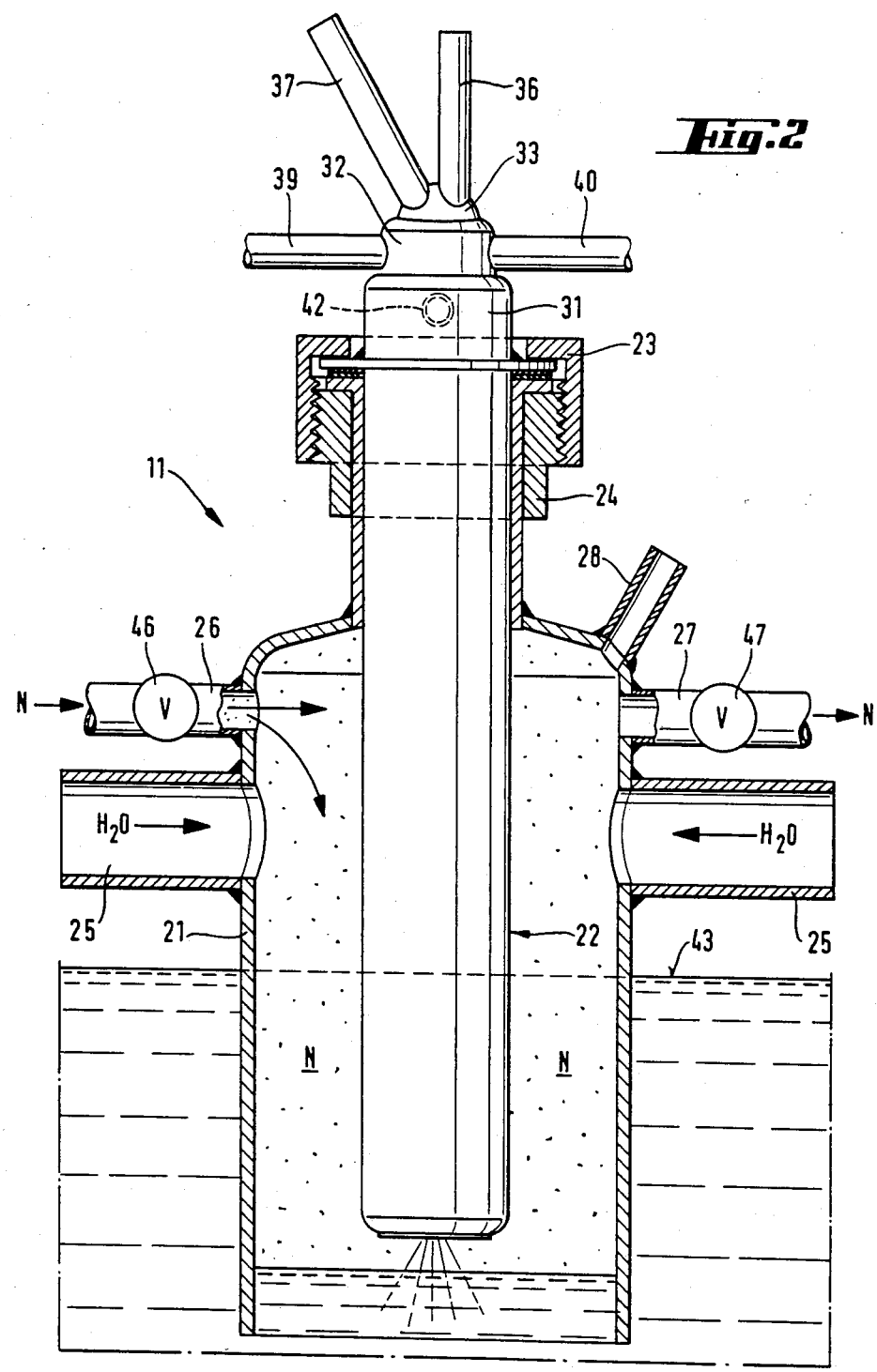

The process according to the invention is preferably performed in the apparatus according to the invention. An embodiment example of such an apparatus is further illustrated in the following with the aid of drawings. These show:

FIG. 1: a schematic general view of the apparatus,

FIG. 2: a spray arrangement in a sectional detail view,

FIG. 3: a longitudinal cross section through the actual spray nozzle of FIG. 2, and FIG. 4: a cross section through the spray nozzle along line A—A of FIG. 3.

The apparatus comprises, as illustrated by the drawings, two circulation systems, namely, a melt circulation system SMK and a suspension circulation system SUK. The melt circulation system contains a melting vessel (1) for the cyanuric chloride, a filter (2), a metering (and circulating) pump (3) and a pressure maintaining valve (4), as well as various pipe lines, which are not described in any greater detail, for connecting together the components mentioned. The suspension circulation system SUK includes a crystallizer (water tank) (5), a mill (6), a circulating pump (7) and a cooler (8), as well as likewise connecting pipes not designated. There are also provided a supply pipe (9) for supplying a liquid phase (water or aqueous ammonia or amine solution or suspension) to the crystallizer (5) and a supply pipe (10) for removal of the suspension from the suspension circulation system SUK. Finally, the apparatus includes also, as central element, a spray arrangement (11), which is connected to the melt circulation system SMK, and which serves to spray melt (cyanuric chloride) into the liquid phase contained in the crystallizer (5).

The construction of the spray arrangement (11) is shown in FIG. 2 and FIG. 3. It comprises an immersion cone (21), roughly bottle-shaped and open at the bottom, and a spray nozzle (22), which is arranged coaxially in the cone, and which is secured, in a detachable manner, in the immersion cone by means of a screw cap (23) and a threaded sleeve (24). The immersion cone (21) has, about half way up its height, two water-supply connections (25) located opposite to one another; and roughly above these are two connections (26) and (27) for the supply and removal of pressure gas (nitrogen). There is also provided a connection (28) for a pressure gauge. The nitrogen supply and removal is controlled through two valves (46) and (47).

The actual spray nozzle (22) consists essentially of three coaxial cylinders (31), (32) and (33), which between them form two annular spaces (34) and (35). The most inner cylinder (33) forms the actual nozzle. It has at its upper end a connection (36) for the supply of melt, and a connection (37) for a thermocouple; and into its lower end is screwed a nozzle head (38).

The middle cylinder (32) forms a heating jacket for the nozzle. It is provided with two oppositely situated connections (39) and (40) for a heating medium—usually oil. The annular space (35) between the middle cylinder and the inner cylinder (33) is divided, by a dividing wall (41) extending not fully to the bottom, into two communicating halves, so that the heating medium can flow sufficiently uniformly through the heating jacket. The most outer cylinder (31) forms a thermal insulating jacket for the nozzle, which prevents a heating up of the liquid in which the spray arrangement is immersed when in operation. The outer annular space (34) is for this purpose connected, through a connection (42), to a vacuum source (for example vacuum network or the like).

The entire spray arrangement (11) is suspended by its various supply pipes, and is positioned in relation to the crystallizer (5) in such a manner that the spray nozzle (22) becomes situated below the liquid level (43), that is to say, immersed in the liquid.

The operation of the described apparatus is as follows:

The melted cyanuric chloride is pumped through the filter (2) around the melt circulation system SMK. A partial flow, which is regulated by means of the pressure maintaining valve (4) and the metering pump (3), is fed to the spray arrangement (11), and becomes atinuzed, in water or in an aqueous ammonia or amine solution or suspension, in the crystallizer (5). The contents of the crystallizer are circulated around the suspension circulation system SUK, and are cooled in the process. The mill (6) ensures that any agglomerates present are broken up into fine particles. After the suspension has attained the required solid content, or after the reaction of cyanuric chloride with ammonia or with amines has been completed, a partial flow is continuously removed via the pipe line (10), and is replaced by the corresponding amount of water, or of an aqueous ammonia or amine solution or suspension, by way of supply pipe (9).

In order to start the spraying operation, the nitrogen supply valve (46) is opened and there is consequently formed a cushion of nitrogen in the immersion cone (21); and this cushion then presses the level of the liquid, within the immersion cone, downwards to the extent that the tip of the spray nozzle (22) is no longer immersed. In this condition, the melt feed pipes inside the spray nozzle and also the nozzle tip (of the nozzle head (38)) are heated. The cyanuric chloride melt is now fed into the spray nozzle, and the nitrogen cushion is simultaneously removed by opening of the relief valve (47); the level in the immersion cone is raised as a result, so that the spray nozzle is then immersed in the liquid. It is possible in this manner to prevent a sublimation of the melt and also the escape of hydrolysis products (hydrochloric acid).

By virtue of the control of the level in the immersion cone, it is not necessary for the spray nozzle to be movable, a factor which is advantageous in many respects. This arrangement and the vacuum isolation of the spray nozzle ensure that there is no undesirably large amount of heat transferred to the surrounding liquid. These are essential conditions in the production of cyanuric suspensions, since the required heating temperature is relatively high (160°–190° C.), and the tendency for hydrolysis to occur increases rapidly with rising water temperature.

By means of the water supply connections (25), fresh water or ammonia or amine solution can be fed into the immersion cone (21), so that the immediate surroundings of the spray nozzle (22) can be additionally cooled.

The control of the level of liquid in the immersion cone can be effected by a corresponding opening and closing of the valves (46) and (47), either by hand or by an automatic control system not shown in this case.

The following Examples serve to further illustrate the invention. The term 'parts' denotes parts by weight, and the temperature values are in degrees Centigrade.

EXAMPLE 1

36 parts of melted cyanuric chloride at a temperature of 160° C. are sprayed by means of a pressure nozzle into a dispersion column which is supplied with 108 parts of 2-[(4-amino-2-ureidophenyl)-azo]-naphthalene-3,6,8-trisulfonic acid as a 17% aqueous solution, the method being such that the pressure nozzle is below the level of the liquid. The reaction solution heats up in the process from room temperature to about 30° to 40° C. It is then pumped into a tank where, with maintenance of the pH value at 4 to 4.5 with sodium hydroxide solution, the reaction is completed. Ten minutes after the feeding in of cyanuric choride is finished, the formed dichlorotriazine compound is reacted with ammonia to give the reactive dye of the formula

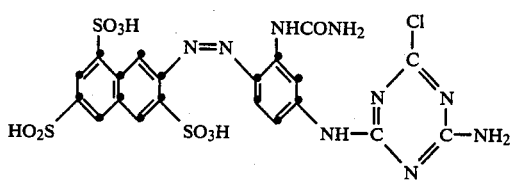

The dye is obtained in a degree of purity equal to that of the dye produced in the customary manner.

EXAMPLE 2

35 parts of a cyanuric chloride melt at 160° C. are sprayed through a pressure nozzle, below the surface, into a dispersion column which is supplied with 60 parts of 1-amino-8-naphthol-3,6-disulfonic acid as a 30% aqueous suspension at 0° C. The reaction mixture heats up during this operation to about 10° C. The mixture is then pumped into a vessel where, at 5° to 10° C. and with maintenance of the pH value at 1.5 to 2.0 with sodium hydroxide solution, the reaction is completed. One hour after the controlled feeding in of cyanuric chloride is finished, no further free amine is detectable. A specimen coupled in the customary manner titrimetrically with a diazonium salt solution shows a yield of over 95% of theory. The dichlorotriazinyl-amino-naphthosulfonic acid thus produced can be used directly to produce reactive dyes.

EXAMPLE 3

60 parts of a cyanuric chloride melt at 160° C. are sprayed through a pressure nozzle, below the surface, into a dispersion column. There are simultaneously fed stoichiometric amounts (½ mol per mol of cyanuric chloride) of a 10% aqueous solution of the sodium salt of 4,4'-diaminostilbene-2,2'-disulfonic acid at a temperature of 0° C. into the said column. The reaction mixture is pumped continuously into a vessel where, at a temperature held at 20° C. with ice, the pH value is kept constant at 4.5 with sodium hydroxide solution. The resulting compound, namely, the disodium salt of N,N'-bis-(4,6-dichloro-1,3,5-triazin-2-yl)-4,4'-diaminostilbene-2,2'-disulfonic acid, can be further processed directly into optical brighteners and gives the customary yields and qualities.

EXAMPLE 4

60 parts of a cyanuric chloride melt are reacted, in the manner described in Example 3, with a 30% aqueous dispersion of the disodium salt of 4,4'-diaminostilbene-2,2'-disulfonic acid. The optical brighteners produced therefrom are obtained in practically quantitative yield.

EXAMPLE 5

45 parts of cyanuric chloride melt at 160° C. are reacted, in a manner analogous to that of Example 3, with 72 parts of a 20% aqueous isopropylamine solution at 0° to 5° C. The formed hydrochloric acid is neutralized in the reaction vessel, at a constant pH value, with about 33 parts of 30% sodium hydroxide solution. After one hour, when virtually no further sodium hydroxide solution is consumed, a complete reaction can be determined analytically (by nitrite salt nitration).

The dichloro-isopropylamino-triazine thus produced is reacted, in the customary manner, with amines, for example, with ethylamine, to obtain herbicides.

EXAMPLE 6

45 parts of a trichlorotriazine melt at 160° C. are sprayed through a pressure nozzle, below the surface, into a dispersion column which is supplied with 21 parts of a 30% aqueous ammonia solution. The reaction mixture is pumped continuously into a vessel where, at about 25° C. with maintenance of the pH value at 8.5 to 9.0 with sodium hydroxide solution, the substitution is completed. The amino-dichlorotriazine obtained in practically quantitative amounts can be used directly to produce a reactive dye.

EXAMPLE 7

60 parts of a trichlorotriazine melt at 160° C. are sprayed through a pressure nozzle, below the surface, into a dispersion column which is supplied with 134 parts of 1,3-phenylenediamine-4-sulfonic acid as a 30% aqueous suspension at 0° C. The reaction mixture warms up in this operation to about 10° C. It is pumped continuously into a vessel where, at 10° C. with maintenance of the pH value at 5.0 with sodium hydroxide solution, the reaction is completed. The 2,4-bis-(3-amino-4-sulfo-anilino)-6-chloro-1,3,5-triazine, which is further processed to give reactive dyes, is obtained in a yield of more than 85%.

EXAMPLE 8

60 parts of a trichlorotriazine melt at 160° C. are sprayed through a pressure nozzle, below the surface, into a dispersion column supplied with 215 parts of water at 3° C. The dispersion column is cooled from the outside so that the liquid does not warm up. A 28% suspension of cyanuric chloride in water is obtained, wherein the particle size of the cyanuric chloride particles is between 0 and 20 μm. The losses in yield caused by hydrolysis are below 0.1%.

What is claimed is:

1. An apparatus for performing a process for producing a suspension of cyanuric chloride in water, or for reacting cyanuric chloride with ammonia or with amines, by bringing melted cyanuric chloride into contact with a liquid phase which is water or an aqueous ammonia or amine solution or suspension, which apparatus comprises a melting vessel provided with heating means, a tank for containing the liquid phase and a melt pipe line having an end which is connected with the melting vessel and an end which is positioned in the tank, the end of the pipe line in the tank being provided with a spray device which comprises an immersion cone and a spray nozzle positioned inside said immersion cone, said cone being connected to a first gas line for supplying a pressurized gas and having a first valve, and to a second gas line for removal of the pressurized gas and having a second valve, the pressurized gas supply and pressurized gas removal being controlled by the first valve and by the second valve so that with the opening of the first valve and the closing of the second valve the level of a liquid phase inside the immersion cone will be controlled so as to sink below the spray nozzle.

2. An apparatus according to claim 1, further including a pressure and metering pump positioned in the melt pipe line.

3. An apparatus according to claim 2, wherein a part of the melt pipe line is included in a circulation system which comprises part of the melt pipe line, a line branching from the melt pipe line after the pressure and metering pump and leading back to the melting vessel, and a pressure maintaining valve in the branch line.

4. An apparatus according to claim 3, wherein the pressure maintaining valve is constructed so as to be adjustable.

5. An apparatus according to claim 1, which further comprises an external circulation system from and to the tank, which external circulation system includes pump means and cooling means.

6. An apparatus according to claim 5, further including a mill positioned in the external circulation system between the tank and the pump means for the external circulation system for breaking up agglomerates.

7. An apparatus according to claim 6, further including a branch outlet pipe extending off the external circulation system after the mill for removal of a suspension.

8. An apparatus according to claim 7, wherein the outlet pipe is arranged after the pump means or the cooling means.

9. An apparatus according to claim 1, wherein the spray nozzle further includes a cylindrical thermal insulating jacket positioned to thermally insulate an outer surface of the nozzle.

10. An apparatus according to claim 9, wherein the spray nozzle further includes a cylindrical heating jacket positioned to effect heating inwardly of the nozzle.

* * * * *